(12) United States Patent
Hansen (10) Patent No.: US 10,770,923 B2
(45) Date of Patent: Sep. 8, 2020

(54) SYSTEMS AND METHODS FOR ELASTIC WIRELESS POWER TRANSMISSION DEVICES

(71) Applicant: TC1 LLC, St. Paul, MN (US)

(72) Inventor: John Freddy Hansen, Pleasanton, CA (US)

(73) Assignee: TC1 LLC, St. Paul, MN (US)

( * ) Notice: Subject to any disclaimer, the term of this patent is extended or adjusted under 35 U.S.C. 154(b) by 3 days.

(21) Appl. No.: 16/222,197

(22) Filed: Dec. 17, 2018

(65) Prior Publication Data

US 2019/0207425 A1    Jul. 4, 2019

Related U.S. Application Data

(60) Provisional application No. 62/613,584, filed on Jan. 4, 2018.

(51) Int. Cl.
*H02J 50/12* (2016.01)
*A61N 1/378* (2006.01)
(Continued)

(52) U.S. Cl.
CPC ............ *H02J 50/12* (2016.02); *A61N 1/3787* (2013.01); *H02J 50/10* (2016.02); *H02J 50/90* (2016.02);
(Continued)

(58) Field of Classification Search
CPC . H02J 50/12; H02J 50/90; H02J 50/10; A61N 1/3787; A61N 1/378; H04B 5/0037;
(Continued)

(56) References Cited

U.S. PATENT DOCUMENTS 4,041,955 A    8/1977  Kelly et al.
4,143,661 A    3/1979  LaForge et al.
(Continued)

FOREIGN PATENT DOCUMENTS

DE    202012000166 U1    4/2013
DE    102012201073 A1    7/2013
(Continued)

OTHER PUBLICATIONS

International Search Report and Written Opinion in International Patent Application No. PCT/US2018/066008, dated Mar. 19, 2019, 15 pages.

(Continued)

*Primary Examiner* — Robert L Deberadinis
(74) *Attorney, Agent, or Firm* — Armstrong Teasdale LLP (57) ABSTRACT

A wireless power transmission device wearable by a subject is provided. The wireless power transmission device includes a power conditioner including a first end and an opposite second end, and a band. The band includes a first end fixedly coupled to the power conditioner first end, a second end fixedly coupled to the power conditioner second end, a body extending between the band first end and the band second end, the body including at least one elastic segment, and a plurality of conductive wires extending along the body to form a plurality of conductive loops, at least one of the plurality of conductive wires electrically coupled to the power conditioner.

20 Claims, 6 Drawing Sheets

(51) Int. Cl.
*H04B 5/00* (2006.01)
*H02J 50/90* (2016.01)
*H02J 50/10* (2016.01)
*H01Q 1/27* (2006.01)

(52) U.S. Cl.
CPC ......... *H04B 5/0037* (2013.01); *H04B 5/0081* (2013.01); *H01Q 1/273* (2013.01)

(58) Field of Classification Search
CPC ........ H04B 5/0081; H04B 5/00; H01Q 1/273; H01Q 1/27
See application file for complete search history.

(56) References Cited

U.S. PATENT DOCUMENTS

| | | | |
|---|---|---|---|
| 4,352,960 A | 10/1982 | Dormer et al. | |
| 4,561,443 A | 12/1985 | Hogrefe et al. | |
| 4,561,444 A | 12/1985 | Livingston et al. | |
| 4,630,615 A | 12/1986 | Yomtov | |
| 4,679,560 A | 7/1987 | Galbraith | |
| 4,726,378 A | 2/1988 | Kaplan | |
| 4,736,747 A | 4/1988 | Drake | |
| 4,924,171 A | 5/1990 | Baba et al. | |
| 4,945,305 A | 7/1990 | Blood | |
| 5,070,223 A | 12/1991 | Colasante | |
| 5,346,458 A | 9/1994 | Affeld | |
| 5,350,413 A | 9/1994 | Miller et al. | |
| 5,569,156 A | 10/1996 | Mussivand | |
| 5,630,836 A | 5/1997 | Prem et al. | |
| 5,690,693 A | 11/1997 | Wang et al. | |
| 5,702,431 A | 12/1997 | Wang et al. | |
| 5,755,748 A | 5/1998 | Borza | |
| 5,771,438 A | 6/1998 | Palermo et al. | |
| 5,831,248 A | 11/1998 | Hojyo et al. | |
| 5,948,006 A | 9/1999 | Mann | |
| 6,123,726 A | 9/2000 | Mori et al. | |
| 6,149,683 A | 11/2000 | Lancisi et al. | |
| 6,212,430 B1 | 4/2001 | Kung | |
| 6,296,533 B1 | 10/2001 | Grubbs et al. | |
| 6,312,338 B1 | 11/2001 | Sato et al. | |
| 6,320,354 B1 | 11/2001 | Sengupta et al. | |
| 6,324,431 B1 | 11/2001 | Zarinetchi et al. | |
| 6,327,504 B1 | 12/2001 | Dolgin et al. | |
| 6,389,318 B1 | 5/2002 | Zarinetchi et al. | |
| 6,400,991 B1 | 6/2002 | Kung | |
| 6,442,434 B1 | 8/2002 | Zarinetchi et al. | |
| 6,451,055 B1 | 9/2002 | Weiss | |
| 6,458,164 B1 | 10/2002 | Weiss | |
| 6,478,820 B1 | 11/2002 | Weiss | |
| 6,553,263 B1 | 4/2003 | Meadows et al. | |
| 6,579,315 B1 | 6/2003 | Weiss | |
| 6,591,139 B2 | 7/2003 | Loftin et al. | |
| 6,605,032 B2 | 8/2003 | Benkowski et al. | |
| 6,647,298 B2 | 11/2003 | Abrahamson et al. | |
| 6,650,213 B1 | 11/2003 | Sakurai et al. | |
| 6,723,039 B2 | 4/2004 | French et al. | |
| 6,772,011 B2 | 8/2004 | Dolgin | |
| 6,801,807 B2 | 10/2004 | Abrahamson | |
| 6,810,289 B1 | 10/2004 | Shaquer | |
| 6,850,803 B1 | 2/2005 | Jimenez et al. | |
| 6,894,456 B2 | 5/2005 | Tsukamoto et al. | |
| 6,895,281 B1 | 5/2005 | Amundson et al. | |
| 6,949,065 B2 | 9/2005 | Sporer et al. | |
| 6,960,968 B2 | 11/2005 | Odendaal et al. | |
| 6,967,621 B1 | 11/2005 | Cadotte, Jr. et al. | |
| 6,985,773 B2 | 1/2006 | Von Arx et al. | |
| 7,015,769 B2 | 3/2006 | Schulman et al. | |
| 7,107,103 B2 | 9/2006 | Schulman et al. | |
| 7,126,310 B1 | 10/2006 | Barron | |
| 7,225,032 B2 | 5/2007 | Schmeling et al. | |
| 7,246,040 B2 | 7/2007 | Borg et al. | |
| 7,286,880 B2 | 10/2007 | Olson et al. | |
| 7,428,438 B2 | 9/2008 | Parramon et al. | |
| 7,471,986 B2 | 12/2008 | Hatlestad | |
| 7,496,733 B2 | 2/2009 | Altman et al. | |
| 7,505,816 B2 | 3/2009 | Schmeling et al. | |
| 7,515,012 B2 | 4/2009 | Schulman et al. | |
| 7,522,878 B2 | 4/2009 | Baarman | |
| 7,532,901 B1 | 5/2009 | Lafranchise et al. | |
| 7,565,187 B1 | 7/2009 | Dynok et al. | |
| 7,571,007 B2 | 8/2009 | Erickson et al. | |
| 7,574,173 B2 | 8/2009 | Terranova et al. | |
| 7,587,241 B2 | 9/2009 | Parramon et al. | |
| 7,599,743 B2 | 10/2009 | Hassler et al. | |
| 7,650,187 B2 | 1/2010 | Gruber et al. | |
| 7,650,192 B2 | 1/2010 | Wahlstrand | |
| 7,711,433 B2 | 5/2010 | Davis et al. | |
| 7,720,546 B2 | 5/2010 | Ginggen et al. | |
| 7,741,734 B2 | 6/2010 | Joannopoulos et al. | |
| 7,761,164 B2 | 7/2010 | Verhoef et al. | |
| 7,774,069 B2 | 8/2010 | Olson et al. | |
| 7,782,190 B1 | 8/2010 | Martin et al. | |
| 7,805,200 B2 | 9/2010 | Kast et al. | |
| 7,812,481 B2 | 10/2010 | Iisaka et al. | |
| 7,818,036 B2 | 10/2010 | Lair et al. | |
| 7,818,037 B2 | 10/2010 | Lair et al. | |
| 7,825,543 B2 | 11/2010 | Karalis et al. | |
| 7,830,114 B2 | 11/2010 | Reed | |
| 7,865,245 B2 | 1/2011 | Torgerson et al. | |
| 7,872,367 B2 | 1/2011 | Recksiek et al. | |
| 7,904,170 B2 | 3/2011 | Harding | |
| 7,932,696 B2 | 4/2011 | Peterson et al. | |
| 7,962,222 B2 | 6/2011 | He et al. | |
| RE42,682 E | 9/2011 | Barreras, Sr. et al. | |
| 8,076,801 B2 | 12/2011 | Karalis et al. | |
| 8,081,925 B2 | 12/2011 | Parramon et al. | |
| 8,096,954 B2 | 1/2012 | Stahmann et al. | |
| 8,140,168 B2 | 3/2012 | Olson et al. | |
| 8,150,529 B2 | 4/2012 | Snell et al. | |
| 8,165,694 B2 | 4/2012 | Carbanaru et al. | |
| 8,185,212 B2 | 5/2012 | Carbunaru et al. | |
| 8,193,766 B2 | 6/2012 | Rondoni et al. | |
| 8,203,434 B2 | 6/2012 | Yoshida | |
| 8,244,367 B2 | 8/2012 | Wahlstrand et al. | |
| 8,247,926 B2 | 8/2012 | Issa et al. | |
| 8,258,653 B2 | 9/2012 | Kitamura et al. | |
| 8,265,770 B2 | 9/2012 | Toy et al. | |
| 8,278,784 B2 | 10/2012 | Cook et al. | |
| 8,292,052 B2 | 10/2012 | Bohori et al. | |
| 8,299,652 B2 | 10/2012 | Smith et al. | |
| 8,301,079 B2 | 10/2012 | Baarman | |
| 8,319,473 B2 | 11/2012 | Choi et al. | |
| 8,362,742 B2 | 1/2013 | Kallmyer | |
| 8,373,310 B2 | 2/2013 | Baarman et al. | |
| 8,378,522 B2 | 2/2013 | Cook et al. | |
| 8,378,523 B2 | 2/2013 | Cook et al. | |
| 8,463,395 B2 | 6/2013 | Forsell | |
| 8,489,200 B2 | 7/2013 | Zarinetchi et al. | |
| 8,551,163 B2 | 10/2013 | Aber et al. | |
| 8,562,508 B2 | 10/2013 | Dague et al. | |
| 8,581,793 B2 | 11/2013 | Carr | |
| 8,587,154 B2 | 11/2013 | Fells et al. | |
| 8,620,447 B2 | 12/2013 | D'Ambrosio et al. | |
| 8,628,460 B2 | 1/2014 | Yomtov et al. | |
| 8,629,578 B2 | 1/2014 | Kurs et al. | |
| 8,668,473 B2 | 3/2014 | Larose et al. | |
| 8,694,117 B2 | 4/2014 | Aghassian et al. | |
| 8,810,071 B2 | 8/2014 | Sauerlaender et al. | |
| 8,884,468 B2 | 11/2014 | Lemmens et al. | |
| 8,909,351 B2 | 12/2014 | Dinsmoor et al. | |
| 8,971,958 B2 | 3/2015 | Frikart et al. | |
| 9,002,468 B2 | 4/2015 | Shea et al. | |
| 9,106,083 B2 | 8/2015 | Partovi | |
| 9,192,704 B2 | 11/2015 | Yomtov et al. | |
| 9,302,093 B2 | 4/2016 | Mashiach | |
| 9,515,494 B2 | 12/2016 | Kurs et al. | |
| 9,515,495 B2 | 12/2016 | Kurs et al. | |
| 9,560,787 B2 | 1/2017 | Kallmyer et al. | |
| 2002/0038138 A1 | 3/2002 | Zarinetchi et al. | |
| 2002/0087204 A1 | 7/2002 | Kung et al. | |
| 2002/0093456 A1 | 7/2002 | Sawamura et al. | |
| 2003/0135913 A1 | 7/2003 | Yang | |
| 2003/0171792 A1 | 9/2003 | Zarinetchi et al. | |

(56) References Cited

U.S. PATENT DOCUMENTS

| | | |
|---|---|---|
| 2004/0138725 A1 | 7/2004 | Forsell |
| 2004/0256146 A1 | 12/2004 | Frericks et al. |
| 2005/0006083 A1 | 1/2005 | Chen et al. |
| 2005/0090883 A1 | 4/2005 | Westlund et al. |
| 2005/0288743 A1 | 12/2005 | Ahn et al. |
| 2006/0199997 A1 | 9/2006 | Hassler, Jr. et al. |
| 2006/0271129 A1 | 11/2006 | Tai et al. |
| 2007/0096686 A1 | 5/2007 | Jimenez et al. |
| 2007/0123948 A1 | 5/2007 | Dal Molin |
| 2007/0142696 A1 | 6/2007 | Crosby et al. |
| 2007/0191706 A1 | 8/2007 | Calderon et al. |
| 2008/0009198 A1 | 1/2008 | Marino |
| 2008/0027293 A1 | 1/2008 | Vodermayer et al. |
| 2008/0054638 A1 | 3/2008 | Greene et al. |
| 2008/0100294 A1 | 5/2008 | Rohling et al. |
| 2008/0149736 A1 | 6/2008 | Kim et al. |
| 2008/0167531 A1 | 7/2008 | McDermott |
| 2008/0204181 A1* | 8/2008 | Tolle ............... H01F 38/14 336/110 |
| 2008/0211320 A1 | 9/2008 | Cook et al. |
| 2009/0018616 A1 | 1/2009 | Quick et al. |
| 2009/0051224 A1 | 2/2009 | Cook et al. |
| 2009/0072628 A1 | 3/2009 | Cook et al. |
| 2009/0081943 A1 | 3/2009 | Dobyns et al. |
| 2009/0174264 A1 | 7/2009 | Onishi et al. |
| 2009/0212736 A1 | 8/2009 | Baarman et al. |
| 2009/0226328 A1 | 9/2009 | Morello |
| 2009/0270679 A1 | 10/2009 | Hoeg et al. |
| 2009/0284220 A1 | 11/2009 | Toncich et al. |
| 2010/0019985 A1 | 1/2010 | Bashyam et al. |
| 2010/0033021 A1 | 2/2010 | Bennett |
| 2010/0035453 A1 | 2/2010 | Tronnes et al. |
| 2010/0045114 A1 | 2/2010 | Sample et al. |
| 2010/0063347 A1 | 3/2010 | Yomtov et al. |
| 2010/0066305 A1 | 3/2010 | Takahashi et al. |
| 2010/0069992 A1 | 3/2010 | Aghassian et al. |
| 2010/0109958 A1 | 5/2010 | Haubrich et al. |
| 2010/0114143 A1 | 5/2010 | Albrecht et al. |
| 2010/0122995 A1 | 5/2010 | Thomas et al. |
| 2010/0171368 A1 | 7/2010 | Schatz et al. |
| 2010/0184371 A1 | 7/2010 | Cook et al. |
| 2010/0194334 A1 | 8/2010 | Kirby et al. |
| 2010/0210233 A1 | 8/2010 | Cook et al. |
| 2010/0211134 A1 | 8/2010 | Forsell |
| 2010/0222848 A1 | 9/2010 | Forsell |
| 2010/0222849 A1 | 9/2010 | Forsell |
| 2010/0225174 A1 | 9/2010 | Jiang |
| 2010/0244576 A1 | 9/2010 | Hillan et al. |
| 2010/0253340 A1 | 10/2010 | Corum et al. |
| 2010/0256708 A1 | 10/2010 | Thornton et al. |
| 2010/0277121 A1 | 11/2010 | Hall et al. |
| 2010/0308939 A1 | 12/2010 | Kurs |
| 2010/0314946 A1 | 12/2010 | Budde et al. |
| 2010/0331919 A1 | 12/2010 | Digiore et al. |
| 2011/0025132 A1 | 2/2011 | Sato |
| 2011/0043050 A1 | 2/2011 | Yabe et al. |
| 2011/0046699 A1 | 2/2011 | Mazanec et al. |
| 2011/0101790 A1 | 5/2011 | Budgett |
| 2011/0109263 A1 | 5/2011 | Sakoda et al. |
| 2011/0115431 A1 | 5/2011 | Dunworth et al. |
| 2011/0127848 A1 | 6/2011 | Ryu et al. |
| 2011/0148215 A1 | 6/2011 | Marzetta et al. |
| 2011/0178361 A1 | 7/2011 | Yomtov |
| 2011/0181235 A1 | 7/2011 | Walley et al. |
| 2011/0205083 A1 | 8/2011 | Janna et al. |
| 2011/0234011 A1 | 9/2011 | Yi et al. |
| 2011/0234155 A1 | 9/2011 | Chen et al. |
| 2011/0241436 A1 | 10/2011 | Furukawa |
| 2011/0241750 A1 | 10/2011 | Hill |
| 2011/0245892 A1 | 10/2011 | Kast et al. |
| 2011/0266880 A1 | 11/2011 | Kim et al. |
| 2011/0276110 A1 | 11/2011 | Whitehurst et al. |
| 2011/0278948 A1 | 11/2011 | Forsell |
| 2011/0291489 A1 | 12/2011 | Tsai et al. |
| 2011/0291613 A1 | 12/2011 | Rosik et al. |
| 2011/0295345 A1 | 12/2011 | Wells et al. |
| 2011/0298294 A1 | 12/2011 | Takada et al. |
| 2011/0301667 A1 | 12/2011 | Olson et al. |
| 2011/0313238 A1 | 12/2011 | Reichenbach et al. |
| 2012/0001485 A1 | 1/2012 | Uchida |
| 2012/0032522 A1 | 2/2012 | Schatz et al. |
| 2012/0039102 A1 | 2/2012 | Shinoda |
| 2012/0057322 A1 | 3/2012 | Waffenschmidt |
| 2012/0065458 A1 | 3/2012 | Tol |
| 2012/0080957 A1 | 4/2012 | Cooper et al. |
| 2012/0091951 A1 | 4/2012 | Sohn |
| 2012/0104997 A1 | 5/2012 | Carobolante |
| 2012/0109256 A1 | 5/2012 | Meskins et al. |
| 2012/0119914 A1 | 5/2012 | Uchida |
| 2012/0146575 A1 | 6/2012 | Armstrong et al. |
| 2012/0149229 A1 | 6/2012 | Kearsley et al. |
| 2012/0150259 A1 | 6/2012 | Meskens |
| 2012/0153739 A1 | 6/2012 | Cooper et al. |
| 2012/0153954 A1 | 6/2012 | Ota et al. |
| 2012/0157753 A1 | 6/2012 | D'Ambrosio |
| 2012/0157754 A1 | 6/2012 | D'Ambrosio |
| 2012/0158407 A1 | 6/2012 | Forsell |
| 2012/0161539 A1 | 6/2012 | Kim et al. |
| 2012/0164943 A1 | 6/2012 | Bennett |
| 2012/0169132 A1 | 7/2012 | Choudhary et al. |
| 2012/0169133 A1 | 7/2012 | Lisi et al. |
| 2012/0169137 A1 | 7/2012 | Lisi et al. |
| 2012/0169139 A1 | 7/2012 | Kudo |
| 2012/0169278 A1 | 7/2012 | Choi et al. |
| 2012/0175967 A1 | 7/2012 | Dibben et al. |
| 2012/0235364 A1 | 9/2012 | Wang et al. |
| 2012/0239118 A1 | 9/2012 | Ozawa et al. |
| 2012/0245649 A1 | 9/2012 | Bohori et al. |
| 2012/0245664 A1 | 9/2012 | Smith et al. |
| 2012/0259398 A1 | 10/2012 | Chen et al. |
| 2012/0274148 A1 | 11/2012 | Sung et al. |
| 2012/0306433 A1 | 12/2012 | Kim et al. |
| 2013/0007949 A1 | 1/2013 | Kurs et al. |
| 2013/0060103 A1 | 3/2013 | Bergida et al. |
| 2013/0119773 A1 | 5/2013 | Davis |
| 2013/0127253 A1 | 5/2013 | Stark et al. |
| 2013/0149960 A1 | 6/2013 | Dec et al. |
| 2013/0159956 A1 | 6/2013 | Verghese et al. |
| 2013/0190551 A1 | 7/2013 | Callaway et al. |
| 2013/0197607 A1 | 8/2013 | Wilder et al. |
| 2013/0214731 A1 | 8/2013 | Dinsmoor et al. |
| 2013/0241306 A1 | 9/2013 | Aber et al. |
| 2013/0241468 A1 | 9/2013 | Moshfeghi |
| 2013/0271088 A1 | 10/2013 | Hwang et al. |
| 2013/0289334 A1 | 10/2013 | Badstibner et al. |
| 2013/0310630 A1 | 11/2013 | Smith et al. |
| 2013/0320773 A1 | 12/2013 | Schatz et al. |
| 2013/0331638 A1 | 12/2013 | Cameron et al. |
| 2014/0005466 A1 | 1/2014 | Crosby et al. |
| 2014/0011447 A1 | 1/2014 | Konanur et al. |
| 2014/0028110 A1 | 1/2014 | Petersen et al. |
| 2014/0028111 A1 | 1/2014 | Hansen et al. |
| 2014/0031606 A1 | 1/2014 | Hansen et al. |
| 2014/0073839 A1 | 3/2014 | Yomtov et al. |
| 2014/0152252 A1 | 6/2014 | Wood |
| 2014/0163644 A1 | 6/2014 | Scott et al. |
| 2014/0265620 A1 | 9/2014 | Hoarau et al. |
| 2014/0265621 A1 | 9/2014 | Wong et al. |
| 2014/0275727 A1 | 9/2014 | Bonde et al. |
| 2015/0123654 A1 | 5/2015 | Gagnon et al. |
| 2015/0207330 A1 | 7/2015 | Petersen |
| 2015/0207331 A1 | 7/2015 | Petersen |
| 2015/0222127 A1 | 8/2015 | Hansen et al. |
| 2015/0222128 A1 | 8/2015 | Hansen |
| 2015/0222139 A1 | 8/2015 | Petersen et al. |
| 2015/0229289 A1 | 8/2015 | Suzuki |
| 2015/0290373 A1 | 10/2015 | Rudser et al. |
| 2015/0380355 A1* | 12/2015 | Rogers ............... H01L 23/5389 257/773 |
| 2016/0135684 A1 | 5/2016 | Kappel et al. |
| 2016/0218432 A1 | 7/2016 | Pope et al. |
| 2016/0250484 A1 | 9/2016 | Nguyen et al. |
| 2016/0254703 A1 | 9/2016 | Hansen |
| 2016/0254704 A1 | 9/2016 | Hansen et al. |

(56) References Cited

U.S. PATENT DOCUMENTS

| | | |
|---|---|---|
| 2017/0043077 A1 | 2/2017 | Tuseth et al. |
| 2017/0207824 A1* | 7/2017 | Von Novak, III ...... H04W 4/80 |
| 2018/0078329 A1 | 3/2018 | Hansen et al. |
| 2018/0199635 A1* | 7/2018 | Longinotti-Buitoni ..................... A61B 5/0205 |

FOREIGN PATENT DOCUMENTS

| | | |
|---|---|---|
| EP | 0589608 A2 | 3/1994 |
| EP | 1513241 A1 | 3/2005 |
| EP | 2267864 A2 | 12/2010 |
| GB | 2477034 A | 7/2011 |
| JP | H03109063 A | 5/1991 |
| JP | H11506646 A | 6/1999 |
| JP | 2013094456 A | 5/2013 |
| JP | 2013161640 A | 8/2013 |
| JP | 2014160611 A | 9/2014 |
| KR | 1020020089605 A | 11/2002 |
| KR | 1020120007296 A | 1/2012 |
| KR | 1020120077448 A | 7/2012 |
| WO | 0001442 A2 | 1/2000 |
| WO | 0074747 A1 | 12/2000 |
| WO | 0137926 A1 | 5/2001 |
| WO | 2005106901 A2 | 11/2005 |
| WO | 2007053881 A1 | 5/2007 |
| WO | 2008066941 A2 | 6/2008 |
| WO | 2009018271 A1 | 2/2009 |
| WO | 2009021220 A1 | 2/2009 |
| WO | 2009023905 A1 | 2/2009 |
| WO | 2009042977 A1 | 4/2009 |
| WO | 2010030378 A1 | 3/2010 |
| WO | 2010089354 A2 | 8/2010 |
| WO | 2011081626 A1 | 7/2011 |
| WO | 2011113934 A1 | 9/2011 |
| WO | 2012002063 A1 | 1/2012 |
| WO | 2012045050 A2 | 4/2012 |
| WO | 2012056365 A2 | 5/2012 |
| WO | 2012087807 A2 | 6/2012 |
| WO | 2012087811 A2 | 6/2012 |
| WO | 2012087816 A2 | 6/2012 |
| WO | 2012087819 A2 | 6/2012 |
| WO | 2012099965 A2 | 7/2012 |
| WO | 2012141752 A2 | 10/2012 |
| WO | 2013110602 A1 | 8/2013 |
| WO | 2013138451 A1 | 9/2013 |
| WO | 2014039673 A1 | 3/2014 |
| WO | 2017070372 A1 | 4/2017 |

OTHER PUBLICATIONS

Bonde et al.; Promise of unrestricted mobility with innovative, portable wireless powering of a mechanical circulatory assist device; American Association for Thoracic Surgery; ©2012; 2 pgs.; retrieved Mar. 12, 2014 from the internet: http://aats.org/annualmeeting/Abstracts/2012/T8.cgi.

Chargepoint, Inc.; —chargepoin+®; product brochure; 4 pgs.; ©2014; retrieved Mar. 12, 2014 from the internet: http://www.chargepoint.com/network/.

Dixon, Jr.; Eddy current losses in transformer windings and circuit wiring; Unitrode Corp. Seminar Manual (SEM600); Watertown, MA; 12 pgs.; 1988 (year of pub. sufficiently earlier than effective US filing date and any foreign priority date).

Evatran; PluglessTM Level 2 EV Charging System (3.3kW); product brochure; 7 pgs.; retrieved Mar. 12, 2014 from the Internet: http://www.pluglesspower.com/tech-specs/.

Ferret, B.; Electric vehicles get big boost!; Renewable Energy World; 3 pgs.; Jul. 30, 2012; retrieved Jul. 30, 2012 from the internet: http://www.renewableenergyworld.com/rea/blog/post/2012/07/.

Motavalli, Jim; WiTricity Takes Its Car-Charging Technology Out for a Road Test; New York Times; 3 pgs.; Jul. 25, 2012; retrieved Mar. 12, 2014 from the internet: http://wheels.blogs.nytimes.com/2012/07/25/witricity-takes-its-car-charging-technology-out-for-a-road-test/.

Notification of Transmittal of the International Search Report and the Written Opinion of the International Searching Authority for PCT Application No. PCT/US2015/051474, dated Dec. 30, 2015.

Development and Implementation of RFID Technology, Ed. Cristina Turcu, Feb. 2009, pp. 28-30, 93-97.

Merli, Francesco, et al., "Design, Realization and Measurements of a Miniature Antenna for Implantable Wireless Communication Systems", IEEE Transaction on Antennas and Propagation, vol. 59, No. 10, Oct. 2011, pp. 3544-3555.

Merli, Francesco, et al., "The Effect of Insulating Layers on the Performance of Implanted Antennas", IEEE Transaction on Antennas and Propagation, vol. 59, No. 1, Jan. 2011, pp. 21-31.

Abadia, Javier, et al., 3D-Spiral Small Antenna Design and Realization for Biomdical Telemetry in the MICS Band. Radioengineering, vol. 18, No. 4, Dec. 2009, pp. 359-367.

* cited by examiner

SYSTEMS AND METHODS FOR ELASTIC WIRELESS POWER TRANSMISSION DEVICES

CROSS REFERENCE TO RELATED APPLICATIONS

This application claims priority to provisional application Ser. No. 62/613,584, filed Jan. 4, 2018, which is incorporated herein in its entirety.

INCORPORATION BY REFERENCE

All publications and patent applications mentioned in this specification are herein incorporated by reference to the same extent as if each individual publication or patent application was specifically and individually indicated to be incorporated by reference.

FIELD

This disclosure relates generally to methods and systems for transmitting and receiving power wirelessly, and in particular, an elastic wireless power transmission device wearable by a patient.

BACKGROUND

Powered devices need to have a mechanism to supply power to the operative parts. Typically systems use a physical power cable to transfer energy over a distance. There has been a continuing need for systems that can transmit power efficiently over a distance without physical structures bridging the physical gap.

Systems and methods that supply power without electrical wiring are sometimes referred to as wireless energy transmission (WET). Wireless energy transmission greatly expands the types of applications for electrically powered devices. One such example is the field of implantable medical devices. Implantable medical devices typically require an internal power source able to supply adequate power for the reasonable lifetime of the device or an electrical cable that traverses the skin. Typically an internal power source (e.g., a battery) is feasible for only low power devices like sensors. Likewise, a transcutaneous power cable significantly affects quality of life (QoL), infection risk, and product life, among many drawbacks.

More recently there has been an emphasis on systems that supply power to an implanted device without using transcutaneous wiring. This is sometimes referred to as a Transcutaneous Energy Transfer System (TETS). Frequently, energy transfer is accomplished using two magnetically coupled coils set up like a transformer so power is transferred magnetically across the skin from a transmitter coil to a receiver coil. Conventional systems are relatively sensitive to variations in position and alignment of the coils. In order to provide constant and adequate power, the two coils need to be physically close together and well aligned.

A transmitter coil in a TETS may be relatively heavy, and supporting the weight of a transmitter coil while keeping the transmitter coil aligned with the receiver coil may be relatively difficult, especially when attempting to maintain patient comfort. Further, the transmitter coil may vibrate or migrate over time, impacting power transfer efficiency. In addition, transmitter coils may generate significant amounts of heat.

SUMMARY OF THE DISCLOSURE

In one embodiment, a wireless power transmission device wearable by a subject is provided. The wireless power transmission device includes a power conditioner including a first end and an opposite second end, and a band. The band includes a first end fixedly coupled to the power conditioner first end, a second end fixedly coupled to the power conditioner second end, a body extending between the band first end and the band second end, the body including at least one elastic segment, and a plurality of conductive wires extending along the body to form a plurality of conductive loops, at least one of the plurality of conductive wires electrically coupled to the power conditioner.

In another embodiment, a wireless power transfer system is provided. The wireless power transfer system includes a wireless power receiver configured to be implanted within a subject, and a wireless power transmission device wearable by the subject, the wireless power transmission device configured to wirelessly transmit power to the wireless power receiver. The wireless power transmission device includes a power conditioner including a first end and an opposite second end, and a band. The band includes a first end fixedly coupled to the power conditioner first end, a second end fixedly coupled to the power conditioner second end, a body extending between the band first end and the band second end, the body including at least one elastic segment, and a plurality of conductive wires extending along the body to form a plurality of conductive loops, at least one of the plurality of conductive wires electrically coupled to the power conditioner.

In yet another embodiment, a method of operating a wireless power transfer system is provided. The method includes implanting a wireless power receiver in a subject, and positioning a wireless power transmission device on the subject, the wireless power transmission device including a power conditioner including a first end and an opposite second end, and a band including a first end fixedly coupled to the power conditioner first end, a second end fixedly coupled to the power conditioner second end, a body extending between the band first end and the band second end, the body including at least one elastic segment, and a plurality of conductive wires extending along the body to form a plurality of conductive loops, at least one of the plurality of conductive wires electrically coupled to the power conditioner. The method further includes supplying current to the at least one of the plurality of conductive wires using the power conditioner to wirelessly transfer power from the wireless power transmission device to the wireless power receiver.

BRIEF DESCRIPTION OF THE DRAWINGS

The novel features of the disclosure are set forth with particularity in the claims that follow. A better understanding of the features and advantages of the present disclosure invention will be obtained by reference to the following detailed description that sets forth illustrative embodiments, in which the principles of the invention are utilized, and the accompanying drawings of which:

DETAILED DESCRIPTION

In the description that follows, like components have been given the same reference numerals, regardless of whether they are shown in different embodiments. To illustrate an embodiment(s) of the present disclosure in a clear and concise manner, the drawings may not necessarily be to scale and certain features may be shown in somewhat schematic form. Features that are described and/or illustrated with respect to one embodiment may be used in the same way or in a similar way in one or more other embodiments and/or in combination with or instead of the features of the other embodiments.

The systems and methods in certain embodiments include a wireless power transmission device wearable by a subject. The wireless power transmission device includes a power conditioner fixedly coupled to a band. That is, the power conditioner is not selectively detachable from the band. The band includes a body having at least one elastic segment, and a plurality of conductive wires extending along the body. At least one elastic segment allows the wireless power transmission device to be stretched (e.g., when a subject is putting on, removing, or adjusting the wireless power transmission device).

Wireless Power Transmission System

Power may be transmitted wirelessly by magnetic induction. In various embodiments, the transmitter and receiver are closely coupled.

In some cases "closely coupled" or "close coupling" refers to a system that requires the coils to be very near each other in order to operate. In some cases "loosely coupled" or "loose coupling" refers to a system configured to operate when the coils have a significant spatial and/or axial separation, and in some cases up to distance equal to or less than the diameter of the larger of the coils. In some cases, "loosely coupled" or "loose coupling" refers a system that is relatively insensitive to changes in physical separation and/or orientation of the receiver and transmitter.

In various embodiments, the transmitter and receiver are non-resonant coils. For example, a change in current in one coil induces a changing magnetic field. The second coil within the magnetic field picks up the magnetic flux, which in turn induces a current in the second coil. An example of a closely coupled system with non-resonant coils is described in International Pub. No. WO2000/074747, incorporated herein for all purposes by reference. A conventional transformer is another example of a closely coupled, non-resonant system. In various embodiments, the transmitter and receiver are resonant coils. For example, one or both of the coils is connected to a tuning capacitor or other means for controlling the frequency in the respective coil. An example of closely coupled system with resonant coils is described in International Pub. Nos. WO2001/037926; WO2012/087807; WO2012/087811; WO2012/087816; WO2012/087819; WO2010/030378; and WO2012/056365, and U.S. Pub. No. 2003/0171792, incorporated herein for all purposes by reference.

In various embodiments, the transmitter and receiver are loosely coupled. For example, the transmitter can resonate to propagate magnetic flux that is picked up by the receiver at relatively great distances. In some cases energy can be transmitted over several meters. In a loosely coupled system power transfer may not necessarily depend on a critical distance. Rather, the system may be able to accommodate changes to the coupling coefficient between the transmitter and receiver. An example of a loosely coupled system is described in International Pub. No. WO2012/045050, incorporated herein for all purposes by reference.

Power may be transmitted wirelessly by radiating energy. In various embodiments, the system comprises antennas. The antennas may be resonant or non-resonant. For example, non-resonant antennas may radiate electromagnetic waves to create a field. The field can be near field or far field. The field can be directional. Generally far field has greater range but a lower power transfer rate. An example of such a system for radiating energy with resonators is described in International Pub. No. WO2010/089354, incorporated herein for all purposes by reference. An example of such a non-resonant system is described in International Pub. No. WO2009/018271, incorporated herein for all purposes by reference. Instead of antenna, the system may comprise a high energy light source such as a laser. The system can be configured so photons carry electromagnetic energy in a spatially restricted, direct, coherent path from a transmission point to a receiving point. An example of such a system is described in International Pub. No. WO2010/089354, incorporated herein for all purposes by reference.

Power may also be transmitted by taking advantage of the material or medium through which the energy passes. For example, volume conduction involves transmitting electrical energy through tissue between a transmitting point and a receiving point. An example of such a system is described in International Pub. No. WO2008/066941, incorporated herein for all purposes by reference.

Power may also be transferred using a capacitor charging technique. The system can be resonant or non-resonant. Exemplars of capacitor charging for wireless energy transfer are described in International Pub. No. WO2012/056365, incorporated herein for all purposes by reference.

The system in accordance with various aspects of the disclosure will now be described in connection with a system for wireless energy transfer by magnetic induction. The exemplary system utilizes resonant power transfer. The system works by transmitting power between the two inductively coupled coils. In contrast to a transformer, however, the exemplary coils are not coupled together closely. A transformer generally requires the coils to be aligned and positioned directly adjacent each other. The exemplary system accommodates looser coupling of the coils.

While described in terms of one receiver coil and one transmitter coil, one will appreciate from the description herein that the system may use two or more receiver coils and two or more transmitter coils. For example, the transmitter may be configured with two coils—a first coil to resonate flux and a second coil to excite the first coil. One will further appreciate from the description herein that usage of "resonator" and "coil" may be used somewhat interchangeably. In various respects, "resonator" refers to a coil and a capacitor connected together.

In general, most of the flux from the transmitter coil does not reach the receiver coil. The amount of flux generated by the transmitter coil that reaches the receiver coil is described by "k" and is referred to as the "coupling coefficient." In general, the alignment is adequate if the resulting coupling coefficient k exceeds some minimum threshold $k_{min}$. It is preferable if the alignment results in a coupling coefficient close to an optimum value $k_{opt}$. The optimum value $k_{opt}$ is always larger than the minimum value $k_{min}$, and smaller than or equal to a maximum coupling coefficient value $k_{max}$. In some embodiments, $k_{min}$ is about 0.01, and $k_{max}$ is about 0.2.

In various embodiments, the coils are physically separated. In various embodiments, the separation is greater than a thickness of the receiver coil. In various embodiments, the separation distance is equal to or less than the diameter of the larger of the receiver and transmitter coil.

Because most of the flux does not reach the receiver, the transmitter coil must generate a much larger field than what is coupled to the receiver. In various embodiments, this is accomplished by configuring the transmitter with a large number of amp-turns in the coil.

Since only the flux coupled to the receiver gets coupled to a real load, most of the energy in the field is reactive. The current in the coil can be sustained with a capacitor connected to the coil to create a resonator. The power source thus only needs to supply the energy absorbed by the receiver. The resonant capacitor maintains the excess flux that is not coupled to the receiver.

In various embodiments, the impedance of the receiver is matched to the transmitter. This allows efficient transfer of energy out of the receiver. In this case the receiver coil may not need to have a resonant capacitor.

Figure 1:
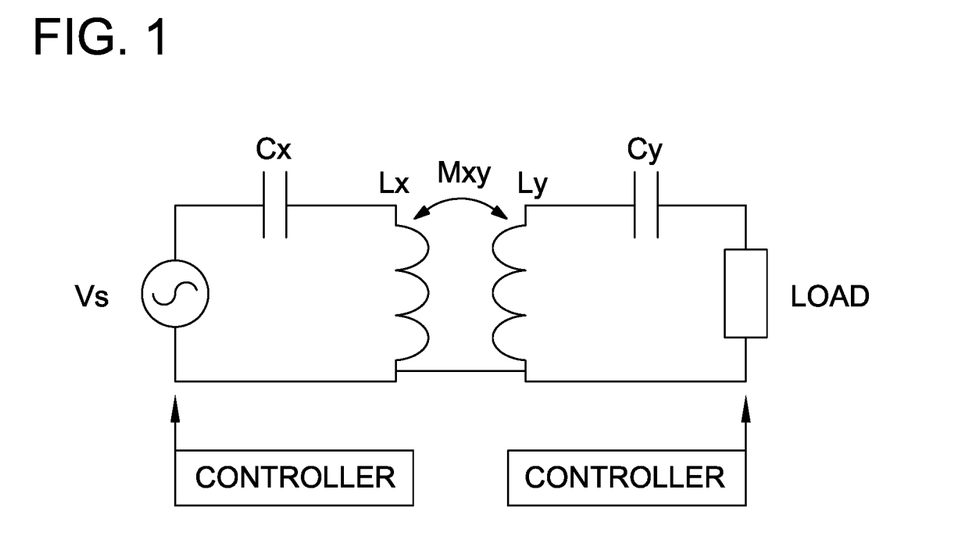
FIG. 1 illustrates a basic wireless power transfer system.

Turning now to FIG. 1, a simplified circuit for wireless energy transmission is shown. The exemplary system shows a series connection, but the system can be connected as either series or parallel on either the transmitter or receiver side.

The exemplary transmitter includes a coil Lx connected to a power source Vs by a capacitor Cx. The exemplary receiver includes a coil Ly connected to a load by a capacitor Cy. Capacitor Cx may be configured to make Lx resonate at a desired frequency. Capacitance Cx of the transmitter coil may be defined by its geometry. Inductors Lx and Ly are connected by coupling coefficient k. Mxy is the mutual inductance between the two coils. The mutual inductance, Mxy, is related to coupling coefficient, k.

$$Mxy = k\sqrt{Lx \cdot Ly}$$

In the exemplary system a power source Vs can be in series with a transmitter coil Lx so it may have to carry all the reactive current. This puts a larger burden on the current rating of the power source and any resistance in the source will add to losses.

The exemplary system includes a receiver configured to receive energy wirelessly transmitted by the transmitter. The exemplary receiver is connected to a load. The receiver and load may be connected electrically with a controllable switch.

In various embodiments, the receiver includes a circuit element configured to be connected or disconnected from the receiver coil by an electronically controllable switch. The electrical coupling can include both a serial and parallel arrangement. The circuit element can include a resistor, capacitor, inductor, lengths of an antenna structure, or combinations thereof. The system can be configured such that power is transmitted by the transmitter and can be received by the receiver in predetermined time increments.

In various embodiments, the transmitter coil and/or the receiver coil is a substantially two-dimensional structure. In various embodiments, the transmitter coil may be coupled to a transmitter impedance-matching structure. Similarly, the receiver coil may be coupled to a receiver impedance-matching structure. Examples of suitable impedance-matching structures include, but are not limited to, a coil, a loop, a transformer, and/or any impedance-matching network. An impedance-matching network may include inductors or capacitors configured to connect a signal source to the resonator structure.

In various embodiments, the transmitter is controlled by a controller (as shown in FIG. 1) and driving circuit. The controller and/or driving circuit may include a directional coupler, a signal generator, and/or an amplifier. The controller may be configured to adjust the transmitter frequency or amplifier gain to compensate for changes to the coupling between the receiver and transmitter.

In various embodiments, the transmitter coil is connected to an impedance-matched coil loop. The loop is connected to a power source and is configured to excite the transmitter coil. The first coil loop may have finite output impedance. A signal generator output may be amplified and fed to the transmitter coil. In use power is transferred magnetically between the first coil loop and the main transmitter coil, which in turns transmits flux to the receiver. Energy received by the receiver coil is delivered by Ohmic connection to the load.

One of the challenges to a practical circuit is how to get energy in and out of the resonators. Simply putting the power source and load in series or parallel with the resonators is difficult because of the voltage and current required. In various embodiments, the system is configured to achieve an approximate energy balance by analyzing the system characteristics, estimating voltages and currents involved, and controlling circuit elements to deliver the power needed by the receiver.

In an exemplary embodiment, the system load power, $P_L$, is assumed to be 15 Watts and the operating frequency, f, is 250 kHz. Then, for each cycle the load removes a certain amount of energy from the resonance:

Energy the load removes in one cycle $$e_L = \frac{P_L}{f} = 60 \ \mu J$$

It has been found that the energy in the receiver resonance is typically several times larger than the energy removed by the load for operative, implantable medical devices. In various embodiments, the system assumes a ratio 7:1 for energy at the receiver versus the load removed. Under this assumption, the instantaneous energy in the exemplary receiver resonance is 420 µJ.

The exemplary circuit was analyzed and the self inductance of the receiver coil was found to be 60 uH. From the energy and the inductance, the voltage and current in the resonator could be calculated.

$$e_y = \frac{1}{2}Li^2$$

$$i_y = \sqrt{\frac{2e_y}{L}} = 3.74A \text{ peak}$$

$$v_y = \omega L_y i_y = 352V \text{ peak}$$

The voltage and current can be traded off against each other. The inductor may couple the same amount of flux regardless of the number of turns. The Amp-turns of the coil needs to stay the same in this example, so more turns means the current is reduced. The coil voltage, however, will need to increase. Likewise, the voltage can be reduced at the expense of a higher current. The transmitter coil needs to have much more flux. The transmitter flux is related to the receiver flux by the coupling coefficient. Accordingly, the energy in the field from the transmitter coil is scaled by k.

$$e_x = \frac{e_y}{k}$$

Given k of 0.05:

$$e_x = \frac{420 \, \mu J}{0.05} = 8.4 \, mJ$$

For the same circuit the self inductance of the transmitter coil was 146 uH as mentioned above. This results in:

$$i_x = \sqrt{\frac{2e_x}{L}} \, 10.7A \text{ peak}$$

$$v_x = \omega L_x i_x = 2460V \text{ peak}$$

One can appreciate from this example, the competing factors and how to balance voltage, current, and inductance to suit the circumstance and achieve the desired outcome. Like the receiver, the voltage and current can be traded off against each other. In this example, the voltages and currents in the system are relatively high. One can adjust the tuning to lower the voltage and/or current at the receiver if the load is lower.

Estimation of Coupling Coefficient and Mutual Inductance

As explained above, the coupling coefficient, k, may be useful for a number of reasons. In one example, the coupling coefficient can be used to understand the arrangement of the coils relative to each other so tuning adjustments can be made to ensure adequate performance. If the receiver coil moves away from the transmitter coil, the mutual inductance will decrease, and all other conditions being equal, less power will be transferred. In various embodiments, the system is configured to make tuning adjustments to compensate for the drop in coupling efficiency.

The exemplary system described above often has imperfect information. For various reasons as would be understood by one of skill in the art, the system does not collect data for all parameters. Moreover, because of the physical gap between coils and without an external means of communications between the two resonators, the transmitter may have information that the receiver does not have and vice versa. These limitations make it difficult to directly measure and derive the coupling coefficient, k, in real time.

Described below are several principles for estimating the coupling coefficient, k, for two coils of a given geometry. The approaches may make use of techniques such as Biot-Savart calculations or finite element methods. Certain assumptions and generalizations, based on how the coils interact in specific orientations, are made for the sake of simplicity of understanding. From an electric circuit point of view, all the physical geometry permutations can generally lead to the coupling coefficient.

Figure 2:
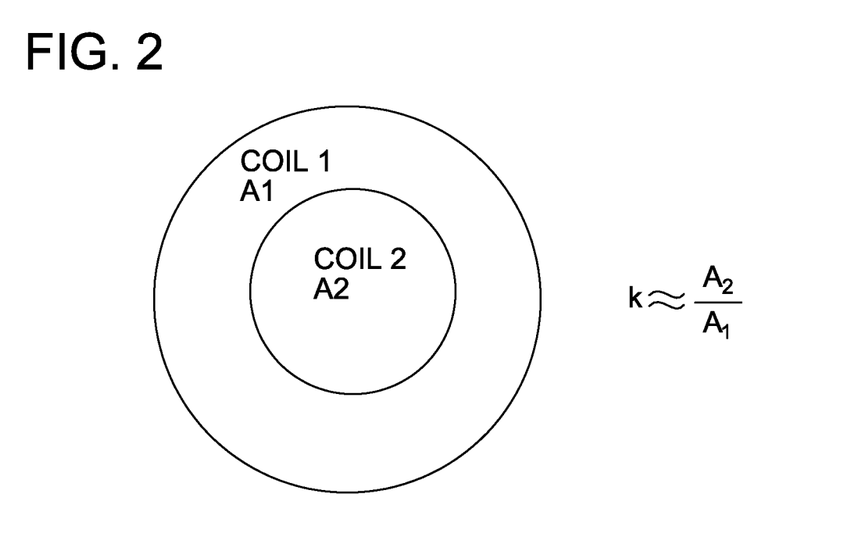
FIG. 2 illustrates magnetic coupling between a pair of coils.

If two coils are arranged so they are in the same plane, with one coil circumscribing the other, then the coupling coefficient can be estimated to be roughly proportional to the ratio of the area of the two coils. This assumes the flux generated by coil 1 is roughly uniform over the area it encloses as shown in FIG. 2.

Figure 3A:
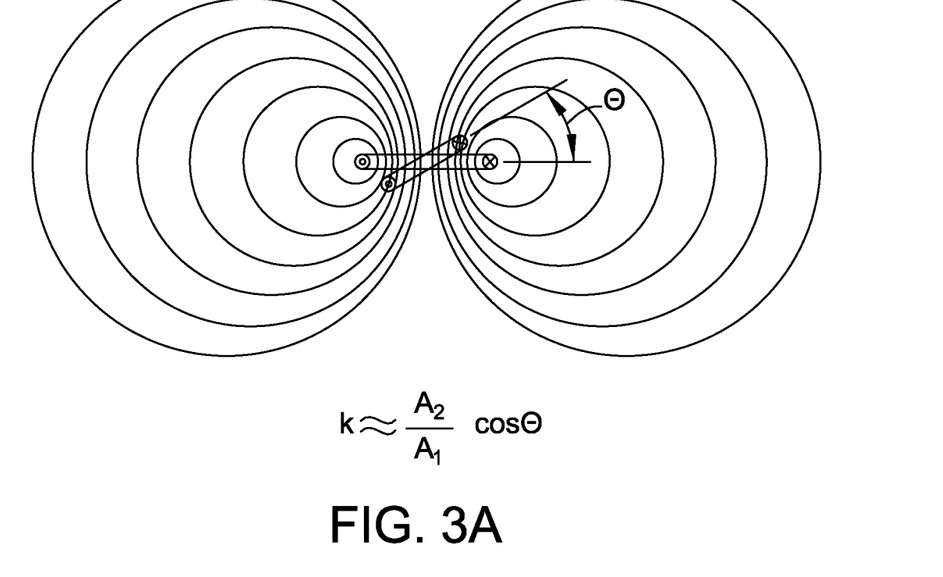
FIGS. 3A and 3B illustrate the effect of coil alignment on the coupling coefficient.

If the coils are out of alignment such that the coils are at a relative angle, the coupling coefficient will decrease. The amount of the decrease is estimated to be about equal to the cosine of the angle as shown in FIG. 3A. If the coils are orthogonal to each other such that theta (θ) is 90 degrees, the flux will not be received by the receiver and the coupling coefficient will be zero.

Figure 3B:
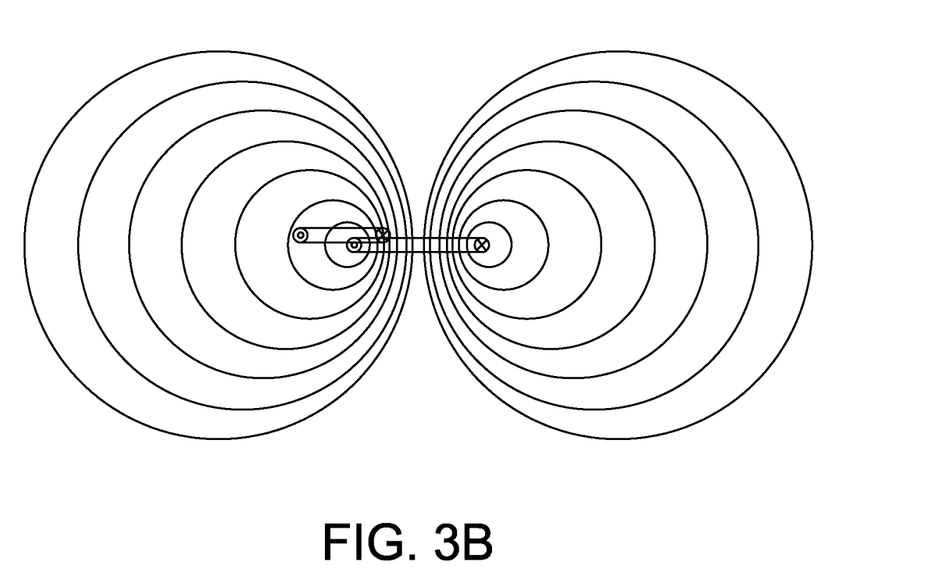

If the coils are arraigned such that half the flux from one coil is in one direction and the other half is in the other direction, the flux cancels out and the coupling coefficient is zero, as shown in FIG. 3B.

A final principle relies on symmetry of the coils. The coupling coefficient and mutual inductance from one coil to the other is assumed to be the same regardless of which coil is being energized.

$$M_{xy} = M_{yx}$$

As described above, a typical TET system can be subdivided into two parts, the transmitter and the receiver. Control and tuning may or may not operate on the two parts independently. For example, as shown in FIG. 1, the transmitter or the receiver or both may include a controller. The goal of this invention is to minimize the effect of relative spatial position and orientation on the magnetic field power transfer rate between a transmitter and a receiver.

Figure 4:
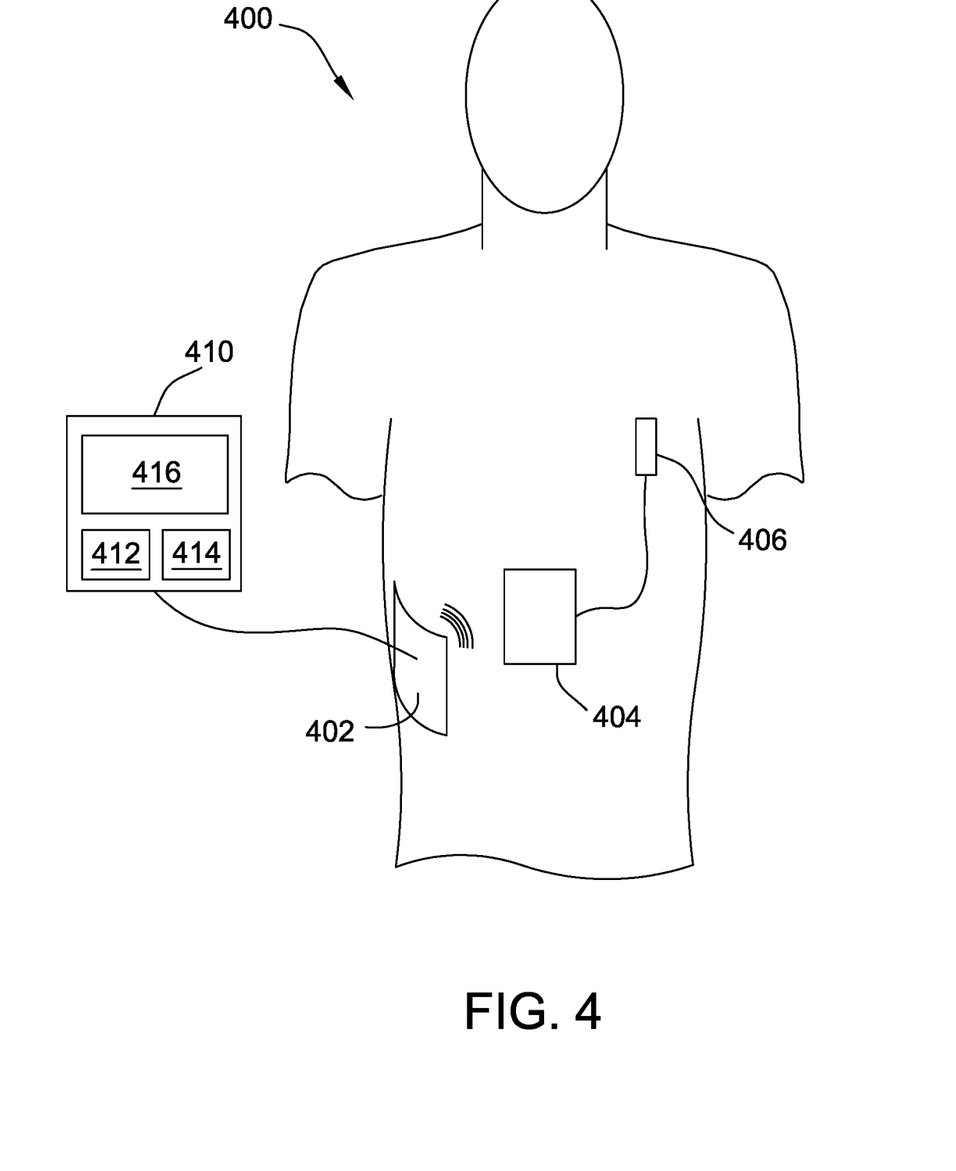
FIG. 4 illustrates a patient placing an external coil to wirelessly transmit power to an implanted coil.

FIG. 4 illustrates one embodiment of a patient 400 using an external coil 402 (a transmitter) to wirelessly transmit power to an implanted coil 404 (a receiver). The implanted coil 404 uses the received power to power an implanted device 406. For example, the implanted device 406 may include a pacemaker or heart pump.

In one embodiment, the external coil 402 is communicatively coupled to a computing device 410, for example, via wired or wireless connection, such that external coil 402 may receive signals from and transmit signals to the computing device 410. In some embodiments, the computing device 410 is a power source for the external coil 402. In other embodiments, the external coil 402 is coupled to an alternative power supply (not shown). The computing device 410 includes a processor 412 in communication with a memory 414. In some embodiments, executable instructions are stored in the memory 414.

The processor 412 may include one or more processing units (e.g., in a multi-core configuration). Further, the processor 412 may be implemented using one or more heterogeneous processor systems in which a main processor is present with secondary processors on a single chip. In another illustrative example, the processor 412 may be a symmetric multi-processor system containing multiple processors of the same type. Further, the processor 412 may be implemented using any suitable programmable circuit including one or more systems and microcontrollers, microprocessors, reduced instruction set circuits (RISC), application specific integrated circuits (ASIC), programmable logic circuits, field programmable gate arrays (FPGA), and any other circuit capable of executing the functions described herein.

In the illustrated embodiment, the memory 414 is one or more devices that enable information such as executable instructions and/or other data to be stored and retrieved. The memory 414 may include one or more computer readable media, such as, without limitation, dynamic random access memory (DRAM), read-only memory (ROM), electrically erasable programmable read-only memory (EEPROM), static random access memory (SRAM), a solid state disk, and/or a hard disk. The memory 414 may be configured to store, without limitation, application source code, application object code, source code portions of interest, object code portions of interest, configuration data, execution events and/or any other type of data.

The computing device 410 further includes a user interface (UI) 416. The UI 416 presents information to a user (e.g., patient 400). For example, the UI 416 may include a display adapter (not shown) that may be coupled to a display device, such as a cathode ray tube (CRT), a liquid crystal display (LCD), an organic LED (OLED) display, and/or an "electronic ink" display. In some embodiments, the UI 416 includes one or more display devices. Further, in some embodiments, presentation interface may not generate visual content, but may be limited to generating audible and/or computer-generated spoken-word content. In the example embodiment, the UI 416 displays one or more representations designed to aid the patient 400 in placing the external coil 402 such that the coupling between the external coil 402 and the implanted coil 404 is optimal. In some embodiments, computing device 410 may be a wearable device. For example, in one embodiment, computing device 410 is a wrist watch, and UI 416 is displayed on the wrist watch.

Figure 5:
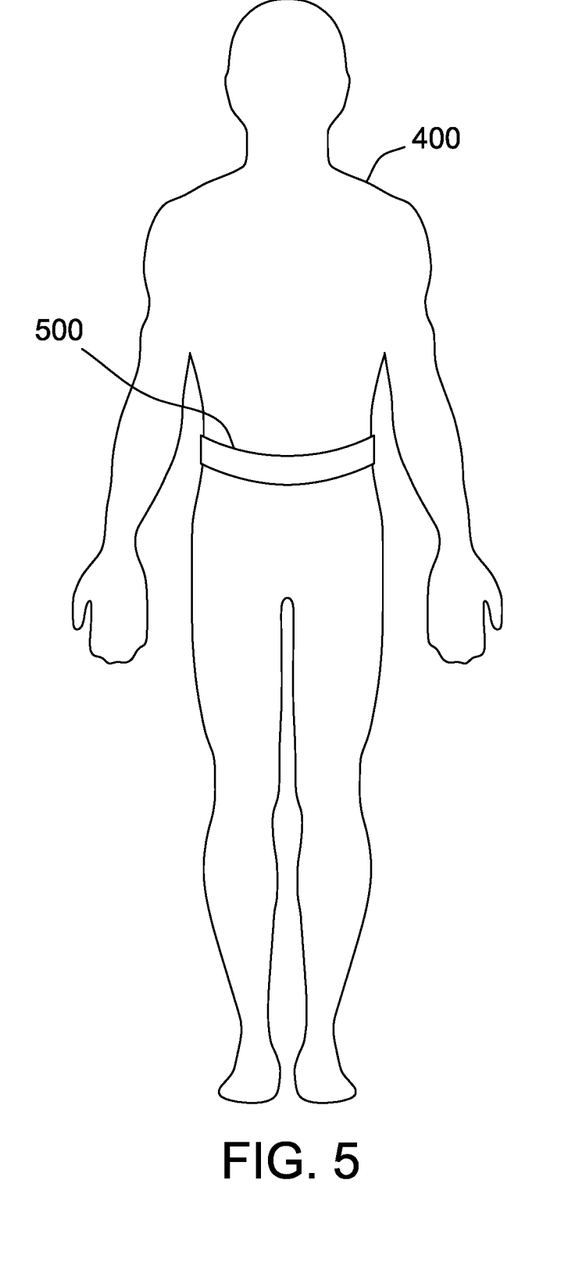
FIG. 5 illustrates an external wireless power transmission device worn by a patient.
Figure 6:
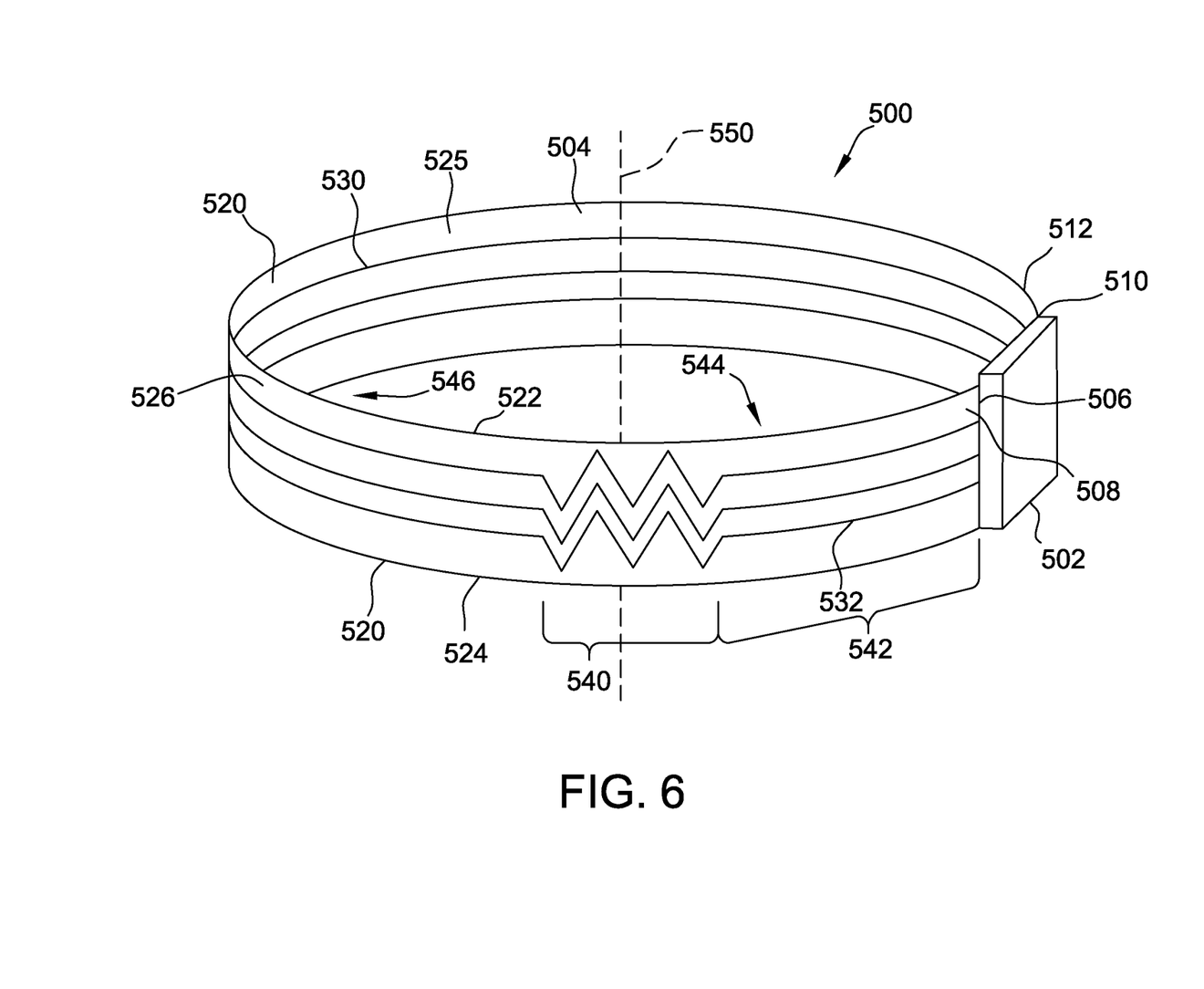
FIG. 6 illustrates the wireless power transmission device shown in FIG. 5.

FIG. 5 is a schematic diagram illustrating one embodiment of an external wireless power transmission device 500 worn by patient 400. Wireless power transmission device 500 may serve as, for example, external coil 402 (shown in FIG. 4). FIG. 6 is a schematic diagram of wireless power transmission device 500. Wireless power transmission device 500 is capable of wirelessly coupling with and transmitting power to an implanted coil, or implanted wireless power receiver device (not shown in FIGS. 4 and 5), such as implanted coil 404 (shown in FIG. 4).

As shown in FIGS. 5 and 6, wireless power transmission device 500 is a generally annular device that may be worn by patient 400 proximate a waist of the patient 400. Accordingly, wireless power transmission device 500 may be worn by patient 400 similar to a belt.

In one embodiment, wireless power transmission device 500 includes a power conditioner 502 and a band 504. Power conditioner 502 and band 504 form a continuous, closed loop. Specifically, a first end 506 of power conditioner 502 is coupled to a first end 508 of band 504, and a second end 510 of power conditioner 502 is coupled to a second end 512 of band 504. Band 504 includes a body 520 that extends between band first end 508 and band second end 512. Further, body 520 includes a first edge 522, and an opposite second edge 524. Body 520 further includes an inner surface 525 and an opposite outer surface 526. Inner and outer surfaces 525 and 526 each extend between first and second edges 522 and 524. When wireless power transmission device 500 is worn by patient 400, inner surface 525 faces inwards towards patient 400 and generally contacts patient 400. Further, when power transmission device 500 is worn by patient 400, outer surface 526 faces outwards, away from patient 400. In some embodiments, wireless power transmission device 500 is stretchable (as described below), and has an unstretched length in a range from approximately 50 cm to 200 cm. Further, wireless power transmission device 500 may have a height (i.e., a distance between first and second edges 522 and 524) in a range from approximately 18 mm to 100 mm, and a thickness in a range from approximately 3 mm to 1 cm. Wireless power transmission device 500 may be stretchable up to 100% (i.e., doubling the length of wireless power transmission device 500), and more particularly, may be stretchable between approximately 20% and 50%. Alternatively, wireless power transmission device 500 may have any suitable dimensions and/or strechability.

As shown in FIG. 6, band 504 includes a plurality of conductive loops 530, or turns. In FIG. 6, three conductive loops 530 are shown for clarity, but those of skill in the art will appreciate that band 504 may include any suitable number of conductive loops 530. For example, band 504 may include at least six conductive loops 530. Each conductive loop 530 is formed by a conductive wire 532, and a single conductive wire 532 may form multiple loops 530. At least some of conductive wires 532 are electrically coupled to power conditioner 502, such that power conditioner 502 is capable of supplying a current to each electrically coupled conductive wire 532. For example, in one embodiment, a first conductive wire 532 forms an exciter coil and a second conductive wire 532 forms a resonator coil. Exciters and resonators are described in U.S. Pat. No. 9,287,040, which is incorporated herein for all purposes by reference.

In this embodiment, the first conductive wire 532 forms at least six conductive loops 530 that constitute the exciter coil, and is electrically coupled at either end to power conditioner 502 (i.e., the first conductive wire 532 bypasses the current supplying components of power conditioner 502 five times). Further, the second conductive wire 532 forms at least six conductive loops 530 that constitute the resonator coil, and is not electrically coupled to power conditioner 502 (i.e., the second conductive wire 532 bypasses the current supplying components of power conditioner 502 every time). Although portions of first and second conductive wires 532 bypass the current supplying components of power conditioner 502, as described above, those portions of first and second conductive wires 532 may still be physically located within a housing of power conditioner 502.

Conductive wires 532 may be, for example, Litz wire including copper cables. Alternatively, conductive wires 532 may be any suitable conductive material. In one embodiment, conductive wires 532 are embedded in body 520. Alternatively, conductive wires 532 may be coupled to inner surface 525 and/or outer surface 526 of body 520.

Band 504 includes at least one elastic segment 540 and at least one inelastic segment 542 in one embodiment. For example, in the embodiment shown in FIG. 6, band 504 includes one elastic segment 540 and two inelastic segments 542. Specifically, a first inelastic segment 544 extends between power conditioner first end 506 and elastic segment 540, and a second inelastic segment 546 extends between elastic segment 540 and power conditioner second end 510. In other embodiments, band 504 may include any suitable number and arrangement of elastic and inelastic segments 540 and 542. For example, band 504 may include a i) single elastic segment 540 and a single inelastic segment 542, ii) a plurality of elastic segments 540 and a single inelastic segment 542, or ii) a plurality of elastic segments 540 and a plurality of inelastic segments 542. As another example, in some embodiments, the entire band 504 is a single elastic segment 540 (i.e., there are no inelastic segments 542).

Elastic segments 540 are generally stretchable, or flexible, and inelastic segments 542 are generally stiff, or inflexible. For example, portions of body 520 corresponding to elastic segments 540 may be made of cross-linked polyethylene, foam material, knitted nylons, polyesters, ariaprene, and/or spandex, and portions of body 520 corresponding to inelastic segments 542 may be made of nylon and/or leather encased in a biothane webbing. In some embodiment, portions of body 520 corresponding to inelastic segments 542 include, for example, stiff plastic plates and/or non-conductive non-magnetic wires (e.g., Kevlar and/or Vectran fibers)

embedded therein to improve stiffness and to prevent patient 400 from folding or twisting band 504. Further, in some embodiments, elastic segments 540 may also include relatively stiff plastic plates (e.g., segments with a cross-sectional aspect ratio from approximately 10:1 to 20:1) and/or non-conductive non-magnetic wires (e.g., Kevlar and/or Vectran fibers) to prevent excessive stretching, allow bending, and provide stiffness against torsion or twisting. In some embodiments, the relatively stiff plastic plates may partially overlap in the unstretched state. Alternatively, portions of body 520 corresponding to elastic and inelastic segments 540 and 542 may be made of any suitable material.

The one or more elastic segments 540 of band 504 allow patient 400 to put on, remove, or adjust a position of wireless power transmission device 500 relatively easily. Specifically, elastic segments 540 allow band 504 to stretch, from a relaxed state to an expanded state, when a sufficient force is applied. Once the force is removed, band 504 returns to the relaxed state. For example, patient 400 may stretch band 504 to put on wireless power transmission device 500 (e.g., by lowering the band over their head or raising the band around their legs), to remove wireless power transmission device 500 (e.g., by raising the band over their head or lowering the band around their legs), or to adjust a current position of wireless power transmission device 500. Further, using one or more elastic segments 540 enables wireless power transmission device 500 to fit patients 400 of different sizes. For example, wireless power transmission device 500 may fit both a larger patient 400 in the expanded state and a smaller patient 400 in the relaxed state.

Because of one or more elastic segments 540, patient 400 is able to put on, remove, or adjust wireless power transmission device 500 without detaching power conditioner 502 and band 504 from one another. Specifically, in one embodiment, power conditioner 502 and band 504 are fixedly attached (i.e., power conditioner 502 and band 504 are not readily detachable from one another). If power conditioner 502 and band 504 were detachably coupled to one another (e.g., with band 504 selectively engageable with power conditioner 502), it would generally require a plurality of electrical connectors to electrically couple wires 532 to power conditioner 502. These electrical connectors would introduce significant resistance into conductive loops 530, which negatively impacts the ability of wireless power transmission device 500 to transfer power. Accordingly, embodiments in which power conditioner 502 is fixedly coupled to band 504 provide substantial advantages over embodiments in power conditioner 502 and band 504 are selectively detachable from one another.

As shown in FIG. 6, each conductive wire 532 extends generally linearly through inelastic segments 542. In contrast, in elastic segment 540, each conductive wire 532 is arranged in a modulating pattern when elastic segment 540 is in the relaxed state. When elastic segment 540 transitions from the relaxed state to the expanded state, wires 532 in elastic segments "straighten out", and more closely resemble a linear shape. When elastic segment 540 is fully stretched (i.e., in a fully expanded state), wires 532 extend substantially linearly through elastic segment 540. In the embodiment shown in FIG. 6, the modulating pattern of each conductive wire 532 is a zigzag pattern. Alternatively, other modulating patterns may be used. For example, wires 532 may be arranged in a sinusoidal wave pattern in some embodiments. Notably, the modulating pattern of wires in elastic segment 540 has been shown to have a relatively small impact on the power transmission capabilities of wireless power transmission device 500.

Wireless power transmission device 500 defines a longitudinal axis 550. To improve power transfer between wireless power transmission device 500 and a wireless power receiver device implanted in patient 400 (such as implanted coil 404 shown in FIG. 4), wireless power transmission device 500 should generally be positioned such that the wireless power receiver device is substantially surrounded by wireless power transmission device 500. Further, longitudinal axis 550 of wireless power transmission device 500 should generally be parallel to a longitudinal axis similarly defined for the wireless power receiver device. In some embodiments, the wireless power receiver device may encircle a rib cage or lung of patient 400. Alternatively, the wireless power receiver device may be implanted within patient 400 at any suitable location.

To facilitate aligning wireless power transmission device 500 with a wireless power receiver device implanted in patient 400, in some embodiments, UI 416 (shown in FIG. 4) displays one or more representations designed to aid patient 400 in positioning power transmission device 500, For example UI 416 may operate in accordance with any of the embodiments described in U.S. patent application Ser. No. 15/709,743, filed Sep. 20, 2017, entitled "SYSTEMS AND METHODS FOR LOCATING IMPLANTED WIRELESS POWER TRANSMISSION DEVICES" which is incorporated herein by reference in its entirety.

In some embodiments, to improve wireless power transfer, a ferrite material (not shown) may be coupled to inner surface 525 and/or outer surface 526 of body 520. The ferrite material external magnetic and/or electrical fields from interfering with operation of wireless power transmission device 500. The ferrite material may include, for example, an array of flexible or inflexible ferrite tiles.

Because wireless power transmission device 500 wraps around patient 400, wireless power transmission device 500 experiences relatively little vibration of migration, improving power transfer. Further, because of the relatively large circumscribed area, any vibration or migration that does occur has relatively little impact. In addition, the relatively large exposed area of wireless power transmission device 500 (i.e., outer surface 526) facilitates dissipating heat generated by wireless power transmission device 500.

Figure 7:
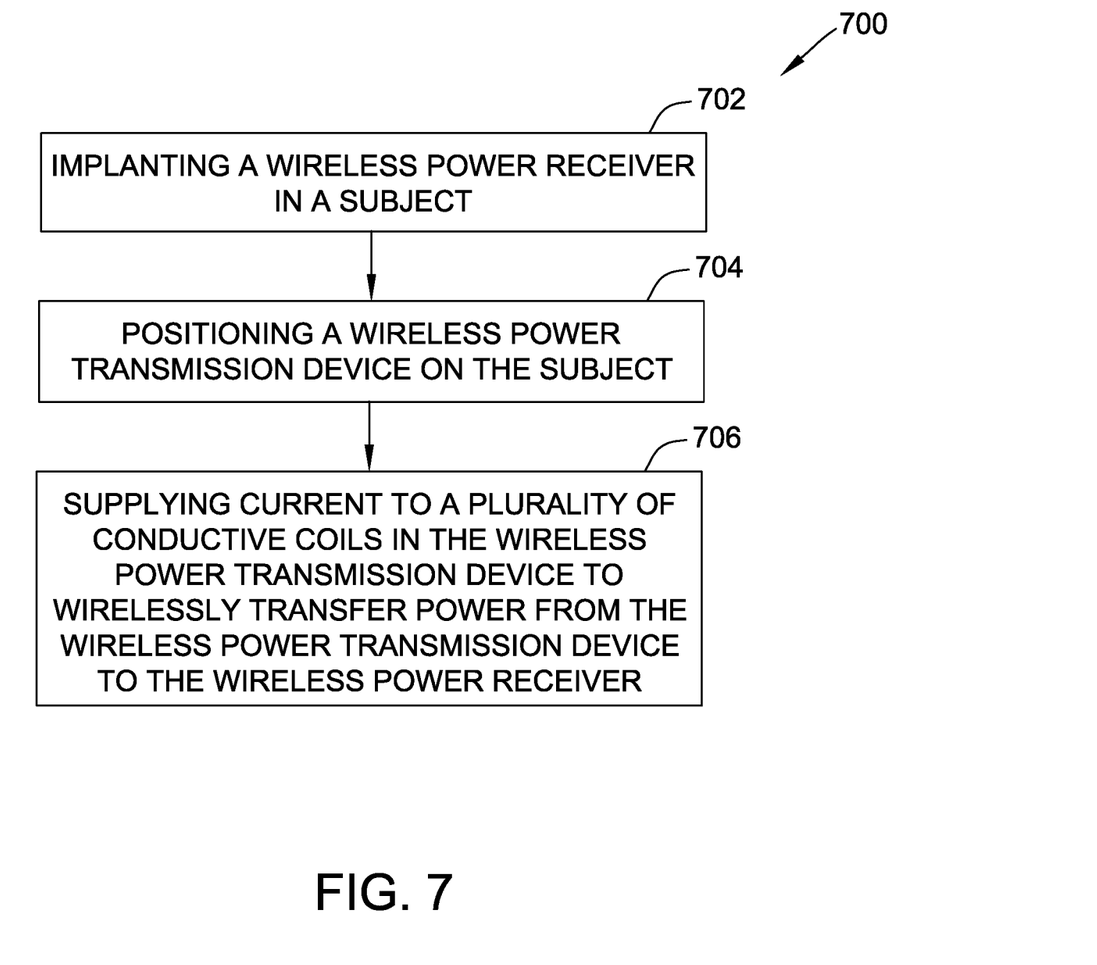
FIG. 7 illustrates a flow chart of one embodiment of a method for operating a wireless power transfer system.

FIG. 7 illustrates a flow chart of one embodiment of a method 700 for operating a wireless power transfer system. Method 700 includes implanting 702 a wireless power receiver, such as implanted coil 404 (shown in FIG. 4) in a subject. Method 700 further includes positioning 704 a wireless power transmission device, such as wireless power transmission device 500 (shown in FIGS. 5 and 6), on the subject. The wireless power transmission device includes a power conditioner and a band. The band includes a body including at least one elastic segment, and a plurality of conductive wires extending along the body, the plurality of conductive wires electrically coupled to the power conditioner. Further, method 700 includes supplying 706 current to the plurality of conductive wires using the power conditioner to wirelessly transfer power from the wireless power transmission device to the wireless power receiver.

Accordingly, using the systems and methods described herein, a wireless power transmission device may be worn, removed, or adjusted by a subject relatively easily. Because the wireless power transmission device includes at least one elastic segment, the wireless power transmission device is stretchable, and does not require any type of detachable coupling mechanism. This allows for easier positioning of the wireless power transmission device, and eliminates the need for components that would otherwise increase resistances in the wireless power transmission device.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents.

What is claimed is:

1. A wireless power transmission device wearable by a subject, the wireless power transmission device comprising:
    a power conditioner comprising a first end and an opposite second end; and
    a band comprising:
        a first end fixedly coupled to the power conditioner first end;
        a second end fixedly coupled to the power conditioner second end;
        a body extending between the band first end and the band second end, the body comprising at least one elastic segment; and
        a plurality of conductive wires extending along the body to form a plurality of conductive loops, at least one of the plurality of conductive wires electrically coupled to the power conditioner.

2. A wireless power transmission device in accordance with claim 1, wherein the at least one elastic segment is stretchable between a relaxed state and an expanded state, and wherein, within the at least one elastic segment, each conductive wire is arranged in a modulating pattern when the at least one elastic segment is in the relaxed state.

3. A wireless power transmission device in accordance with claim 2, wherein the modulating pattern is a zigzag pattern.

4. A wireless power transmission device in accordance with claim 2, wherein, when the at least one elastic segment is in the expanded state, each of the conductive wires extends generally linearly through the at least one elastic segment.

5. A wireless power transmission device in accordance with claim 1, wherein the body further comprises at least one inelastic segment.

6. A wireless power transmission device in accordance with claim 5, wherein the at least one inelastic segment comprises at least one of stiff plates and non-conductive non-magnetic wires embedded in the body.

7. A wireless power transmission device in accordance with claim 1, wherein the body comprises a plurality of elastic segments.

8. A wireless power transfer system comprising:
    a wireless power receiver configured to be implanted within a subject; and
    a wireless power transmission device wearable by the subject, the wireless power transmission device configured to wirelessly transmit power to the wireless power receiver, the wireless power transmission device comprising:
        a power conditioner comprising a first end and an opposite second end; and
        a band comprising:
            a first end fixedly coupled to the power conditioner first end;
            a second end fixedly coupled to the power conditioner second end;
            a body extending between the band first end and the band second end, the body comprising at least one elastic segment; and
            a plurality of conductive wires extending along the body to form a plurality of conductive loops, at least one of the plurality of conductive wires electrically coupled to the power conditioner.

9. A wireless power transfer system in accordance with claim 8, wherein the at least one elastic segment is stretchable between a relaxed state and an expanded state, and wherein, within the at least one elastic segment, each conductive wire is arranged in a modulating pattern when the at least one elastic segment is in the relaxed state.

10. A wireless power transfer system in accordance with claim 9, wherein the modulating pattern is a zigzag pattern.

11. A wireless power transfer system in accordance with claim 9, wherein, when the at least one elastic segment is in the expanded state, each of the conductive wires extends generally linearly through the at least one elastic segment.

12. A wireless power transfer system in accordance with claim 8, wherein the body further comprises at least one inelastic segment.

13. A wireless power transfer system in accordance with claim 12, wherein the at least one inelastic segment comprises at least one of stiff plates and non-conductive non-magnetic wires embedded in the body.

14. A wireless power transfer system in accordance with claim 8, wherein the body comprises a plurality of elastic segments.

15. A wireless power transfer system in accordance with claim 8, further comprising a computing device communicatively coupled to the wireless power transmission device, the computing device comprising a user interface configured to display information that assists the subject in positioning the wireless power transmission device to increase power transmitted to the wireless power receiver.

16. A method of operating a wireless power transfer system, the method comprising:
    implanting a wireless power receiver in a subject;
    positioning a wireless power transmission device on the subject, the wireless power transmission device including a power conditioner including a first end and an opposite second end, and a band including a first end fixedly coupled to the power conditioner first end, a second end fixedly coupled to the power conditioner second end, a body extending between the band first end and the band second end, the body including at least one elastic segment, and a plurality of conductive wires extending along the body to form a plurality of conductive loops, at least one of the plurality of conductive wires electrically coupled to the power conditioner; and
    supplying current to the at least one of the plurality of conductive wires using the power conditioner to wirelessly transfer power from the wireless power transmission device to the wireless power receiver.

17. A method in accordance with claim 16, wherein positioning a wireless power transmission device comprises positioning a wireless power transmission device in which the at least one elastic segment is stretchable between a relaxed state and an expanded state, and wherein, within the at least one elastic segment, each conductive wire is arranged in a modulating pattern when the at least one elastic segment is in the relaxed state.

18. A method in accordance with claim 17, wherein the modulating pattern is a zigzag pattern.

19. A method in accordance with claim 17, wherein, when the at least one elastic segment is in the expanded state, each of the conductive wires extends generally linearly through the at least one elastic segment.

20. A method in accordance with claim 16, wherein positioning a wireless power transmission device comprises positioning a wireless power transmission device in which the body further comprises at least one inelastic segment.

* * * * *